United States Patent [19]

Broad

[11] 4,252,789

[45] Feb. 24, 1981

[54] DEODORANT STICK

[75] Inventor: Reginald W. Broad, Maidenhead, England

[73] Assignee: The Gillette Company, Boston, Mass.

[21] Appl. No.: 62,803

[22] Filed: Aug. 1, 1979

Related U.S. Application Data

[63] Continuation of Ser. No. 918,372, Jun. 23, 1978, abandoned.

[51] Int. Cl.³ .................. A61K 7/32; A61K 31/055
[52] U.S. Cl. ........................ 424/65; 424/DIG. 5; 424/347
[58] Field of Search .............. 424/65, DIG. 5, 347

[56] References Cited

U.S. PATENT DOCUMENTS

| | | | |
|---|---|---|---|
| 2,054,989 | 9/1936 | Moore | 424/DIG. 5 |
| 2,819,995 | 1/1958 | Wassell | 424/DIG. 5 |
| 2,857,315 | 10/1958 | Teller | 424/DIG. 5 |
| 2,900,306 | 8/1959 | Slater | 424/DIG. 5 |
| 2,933,433 | 4/1960 | Teller et al. | 424/DIG. 5 |
| 2,948,684 | 8/1960 | Thiele | 424/DIG. 5 |
| 3,255,082 | 6/1966 | Barton | 424/DIG. 5 |
| 3,259,513 | 7/1966 | Dickson et al. | 424/DIG. 5 |
| 3,576,776 | 4/1971 | Muszik et al. | 424/DIG. 5 |
| 3,708,435 | 1/1973 | Starkman | 424/DIG. 5 |
| 4,011,311 | 3/1977 | Noomen et al. | 424/DIG. 5 |

FOREIGN PATENT DOCUMENTS

| | | | |
|---|---|---|---|
| 802346 | 6/1951 | Fed. Rep. of Germany | 424/DIG. 5 |
| 956099 | 1/1957 | Fed. Rep. of Germany | 424/65 |
| 1230884 | 5/1971 | United Kingdom | 424/DIG. 5 |

OTHER PUBLICATIONS

Chem. Abs., 1951, vol. 45, p. 5372(d).
Chem. Abs., vol. 53, 1959, p. 6547(g)
Cosmetics & Toiletries, 1977, vol. 92. pp. 54–64.

*Primary Examiner*—Dale R. Ore
*Attorney, Agent, or Firm*—Richard A. Wise; Mandel E. Slater

[57] ABSTRACT

An aqueous soap-based deodorant stick consisting essentially of a mixture of sodium stearate and sodium palmitate, a soap-compatible germicide, polyethylene imine or ethoxylated polyethylene imine, and water. A soap-compatible perfume, talc, propylene glycol, glycerin, and wool wax alcohols are optional ingredients.

9 Claims, No Drawings

DEODORANT STICK

This is a continuation of application Ser. No. 918,372, filed June 23, 1978, now abandoned.

BACKGROUND OF THE INVENTION

1. Field of the Invention

This invention relates to deodorant sticks, and more particularly, to soap-based deodorant sticks.

2. Description of the Prior Art

Soap-based stick compositions for applying active ingredients to the skin are well known in the prior art. For instance, U.S. Pat. No. 2,900,306, discloses a deodorant cosmetic stick prepared by gelling a major amount of an alcohol of two to three carbon atoms by the addition of a minor amount of sodium stearate. A deodorant is added to this base, followed by the addition of from about 0.5% to 5% by weight of a water-soluble soap of myristic acid to improve the yielding properties of the stick. Similar sticks are described in U.S. Pat. Nos. 2,857,315 and 2,933,433, which disclose antiperspirant sticks having a base prepared by adding sodium stearate to either propylene glycol or alcohol. Using a glycol or alcohol in such a stick increases the cost considerably. Accordingly, if a less expensive alternative solvent could be found, it would be preferred.

One potential alternative solvent is water. Using water to form a stick is known in the prior art. For instance, U.S. Pat. No. 3,576,776, describes adhesive applicator crayons where the gelling component is a salt formed by combining an aliphatic carboxylic acid having from 8 to 36 carbon atoms with a cation selected from alkali metals, ammonium and lower alkyl ammonium. This salt is added to water, either alone or in combination with a water-miscible organic solvent, producing a gel to which an adhesive component is added. The preferred cation-carboxylic acid combination is sodium stearate.

A stick produced by gelling water with either sodium stearate or sodium palmitate lacks the necessary cosmetic attributes for applying active ingredients to human skin. Sodium palmitate produces a stick with excessive softness and poor heat ageing. Similarly, a stick produced from sodium stearate leaves a film on the skin which is flaky and lacks uniformity and smoothness. Furthermore, adding germicides and fragrances introduces additional problems such as stickiness and softness.

To a large extent, the problems described above are solved when a deodorant stick containing a germicide is produced by gelling water with a mixture of sodium stearate and sodium palmitate in a particular weight-ratio range. However, such a composition expands upon cooling, making the resulting stick difficult to extrude from its packaging. In addition, at temperatures in excess of 35° C., such a stick begins to melt.

Accordingly, a need exists for means for reducing the tendency of such a stick to bind in its packaging and increasing such a stick's high temperature stability.

SUMMARY OF THE INVENTION

The present invention is a water-based deodorant stick consisting essentially of from about 3% to about 10% by weight of a mixture of sodium stearate and sodium palmitate in a weight-ratio range from about 1:1 to about 9:1, from about 0.1% to about 3.0% by weight of a soap-compatible germicide, from about 0.1% to about 0.5% by weight of a compound selected from the class consisting of polyethylene imine and ethoxylated polyethylene imine, said compound having an average molecular weight from about 40,000 to about 100,000, and the balance being water. Adding polyethylene imine or ethoxylated polyethylene imine causes the resulting stick to shrink slightly on setting up, rather than expanding as would occur without the added ingredient. Consequently, such a stick is more readily extruded from the cylindrical case typically used for deodorant sticks. Furthermore, the temperature stability of the resulting stick is enhanced.

DETAILED DESCRIPTION OF THE INVENTION

The deodorant stick of the present invention consists essentially of four basic parts: a mixture of sodium stearate and sodium palmitate, a soap-compatible germicide, polyethylene imine or ethoxylated polyethylene imine, and water. Optional ingredients include a soap-compatible perfume, talc, glycerin, propylene glycol, and a wool wax alcohol.

As stated above, a deodorant stick containing only sodium stearate or sodium palmitate is unacceptably brittle, flaky, or soft, resulting in excessive, nonuniform, or flaky lay-down or melting when exposed to higher temperatures. To overcome these difficulties, a mixture of stearate to palmitate within a certain range is used to give the stick the desired hardness and lay-down characteristics. An acceptable stick is produced as long as the weight ratio range of stearate to palmitate falls between about 1:1 to about 9:1. Outside of that range, an unacceptably soft or hard stick is produced. Stearate to palmitate ratios as low as 1:1 can be used if an additional ageing step, to be described below, is included during preparation of the stick. Accordingly, the broad range of stearate to palmitate is from 9:1 to 1:1, preferably 3.5:1 to 2:1, and more preferably 3.25:1 to 2.75:1. Depending on the particular ratio of stearate to palmitate, an acceptable stick is formed when the total concentration of soap is between about 3% and about 10% by weight. The preferred concentration is between about 6% and about 8% by weight with an excellent stick resulting when 7% be weight of a soap with a stearate to palmitate ratio between about 2.75:1 and about 3.25:1 is used to make a stick.

The sodium stearate and sodium palmitate used in the present invention are typically triple pressed or its equivalent in high purity. Small amounts of the salts of myristic and oleic acid are typically present in commercially available materials. While sodium myristate in concentrations below 5% by weight of the total soap concentration have little effect upon the stick, sodium oleate should be avoided as much as possible and should typically not be present in concentrations in excess of about 2% by weight of the total soap concentration.

The second ingredient of the composition is a soap-compatible germicide. By soap-compatible is meant that the germicide chosen does not interact with the soap base to significantly reduce the germicidal activity of the germicide. Classes of germicides useful in the practice of the present invention include halogenated bisphenols, halogenated aromatic anilides, halogenated carbanalides, phenol derivatives, germicidally-active guanidine derivatives, pyridine derivatives, dioxane derivatives, germicidally-active amphoteric surface-active compounds, inorganic mercuric salts, and germicidally-active nitrofuranyl derivatives. The germicide is typically employed in concentrations by weight from 0.1% to about 3.0%. Alcohol-based deodorant sticks typically need germicide concentrations of only about 0.05% since the alcohol used to form the stick also acts as a germicide. Accordingly, it is preferred that at least 0.2% of a germicide be incorporated in the present invention to obtain the same germicidal efficacy exhibited by alcohol-based deodorant sticks.

The third ingredient of the composition is either polyethylene imine or ethoxylated polyethylene imine having an average molecular weight from about 40,000 to about 100,000. Deodorant sticks are typically dispensed from generally cylindrical cases by the user pushing the stick upward out of the case as the stick becomes worm away from use. During production of the sticks, the heated composition is most conveniently packaged by pouring it into the case to be used by the consumer where it cools and sets up as a solid stick. A stick containing only soap, a germicide, and water expands upon cooling causing the stick to bind within its case. Adding either polyethylene imine or ethoxylated polyethylene imine to the composition causes the stick to shrink slightly on cooling thereby reducing the chances of the stick binding in its case. In addition, when polyethylene imine or ethoxylated polyethylene imine is added to the basic composition, the softening which occurs in warmer climates is greatly reduced. Polyethylene imine or ethoxylated polyethylene imine are typically employed in concentrations by weight from about 0.1% to about 0.5%.

The final main ingredient of the present invention is water. It is preferred that deionized water be used to insure that no metal ions are present which might interfere with the solubility of the sodium salt. Water is used to make up the balance of the composition to 100%.

Since it is desirable to not only prevent odor from forming, but also to mask whatever odor is produced in spite of the germicide, it is desirable to include a soap-compatible perfume. Again, by soap-compatible is meant that the interaction between the soap and the perfume is negligible. Perfume bases useful in the present invention will be readily apparent to those skilled in the art. These will typically be employed in a range from about 0.5% to about 2.0% by weight of the total composition, preferably, at approximately 1% by weight.

As discussed above, one disadvantage of prior art water-based soap sticks is their tendency to melt when temperatures exceed 25° C. While the present invention solves that problem to a great extent, the composition's heat stability can be increased even further by the addition of from about 1% to about 3% by weight of talc. Other optional ingredients include glycerin and propylene glycol. When added to a stick in concentrations up to about 3% by weight, they retard dryout of the stick and act as moisturizers and emollients on the skin. Another optional ingredient is a wool wax alcohol. Adding such alcohols from about 0.2% to about 1.0% by weight reduces any tendency of the stick to dry out and emulsifies the composition giving it a smoother feel when applied to the skin.

Two procedures are available for preparing sticks according to the present invention. By the first procedure, sticks are prepared from commercially available sodium stearate and sodium palmitate. Alternatively, the sodium salts of stearic and palmitic acid may be formed in solution before proceeding to prepare the sticks.

In the first procedure, deionized water at room temperature is mechanically agitated while the sodium salts are added slowly, so that clumping does not occur. The batch is then heated to 67°-71° C. When the solution becomes water clear, indicating that the salts have totally dissolved, perfume, talc, glycerin, propylene glycol, or wool wax alcohols, if desired, are added and dissolved. Next, the germicide is added and dissolved. Polyethylene imine or ethoxylated polyethylene imine is then added. Finally, the composition is poured into molds to cool. It is often desirable to age the sticks for between 8 and 24 hours at between 40° C. and 45° C., preferably 16 hours at 45° C., to increase their hardness. The ageing process is needed more as the proportion of palmitate is increased, and is particularly useful when the stearate to palmitate ratio falls between about 1:1 and about 2:1. Conversely, as the proportion of stearate increases, the need for ageing decreases.

The second procedure begins with the free acids and forms the sodium salt during the process. In this procedure, stearic acid and palmitic acid are added to water along with sodium hydroxide. The ingredients are refluxed for 30 minutes, cooled to 60° C., a germicide, and a perfume, talc, glycerin, propylene glycol or wool wax alcohols are added, if desired. Finally polyethylene imine or ethoxylated polyethylene imine is added. The composition is stirred for 30 minutes, and then poured into molds. Depending on the ratio of stearate to palmitate, it may be desirable to age the composition as described in the first procedure.

The following examples are given by way of illustration only and are not to be considered as limiting the scope of the invention.

EXAMPLE I 7 g of a mixture containing 73% sodium stearate and 26% sodium palmitate is added slowly with stirring to 91.6 g of deionized water to room temperature. The composition is heated to 68° C. until the solution becomes water clear indicating that all the salts have dissolved. To the solution is then added 0.2 grams of 5-chloro-2-(2,4-dichlorophenoxy)phenol, a halogenated bisphenol germicide. 0.2 g of polyethylene imine having an average molecular weight of 60,000 is added and dissolved. The material is then poured into dispensing containers and allowed to cool. The resulting stick provides good deodorant action and lays down an acceptable amount of material when applied to human skin. The stick does not bind in the case and does not soften appreciably until temperatures above 35° C. are reached.

EXAMPLE II 5.2 g of stearic acid, 1.3 g of palmitic acid, and 0.87 g of sodium hydroxide flake were added to 91.2 g of deionized water. The ingredients were held at reflux for 30 minutes and cooled to 60° C., after which 0.2 of 5-chloro-2-(2,4-dichlorophenoxy)phenol, 1 g of 843J perfume (International Flavors and Fragrances, Inc., New York, NY), 0.2 g of ethoxylated polyethylene imine having an average molecular weight of 60,000, and 0.5 g of lanolin alcohols (Super Hartolan, Croda Chemicals Ltd., Cowick Hall, Snaith Goole, North Humberside, DN149AA, England) were added and the composition stirred for 30 minutes. The composition was then poured into cases and allowed to cool to room temperature. The stick composition acts as a deodorant when applied to the skin. It has acceptable lay-down characteristics, doesn't bind in the case, and doesn't soften appreciably until temperatures above 35° C. are reached.

EXAMPLE III

Example II is repeated using the following ingredients:

| Ingredients | Grams |
|---|---|
| Stearic Acid | 4.00 |
| Palmitic Acid | 1.00 |
| Sodium Hydroxide | 0.67 |
| 843J Perfume | 1.00 |
| Lanolin Alcohols | 0.50 |
| 5-chloro-2-(2,4-dichlorophenoxy)phenol | 0.20 |
| Polyethylene Imine (M.W. 60,000) | 0.20 |
| Water | q.s. to 100 |

What is claimed is:

1. A water-based deodorant stick consisting essentially of:
   (a) from about 3% to about 10% by weight of sodium stearate and sodium palmitate having a weight-ratio of stearate to palmitate of about 1:1 to about 9:1;
   (b) from about 0.1% to about 3.0% by weight of a soap-compatible germicide;
   (c) from about 0.1% to about 0.5% by weight of a compound selected from the class consisting of polyethylene imine and ethoxylated polyethylene imine, said compound having an average molecular weight from about 40,000 to about 100,000; and
   (d) the balance being water.

2. A water-based deodorant stick as claimed in claim 1, further including from about 0.2% to about 1.0% by weight of a wool wax alcohol.

3. A water-based deodorant stick as claimed in claim 1, further including from about 0.5% to about 2.0% by weight of a soap-compartible perfume.

4. A water-based deodorant stick as claimed in claim 1, further including from about 1% to about 3% by weight of talc.

5. A water-based deodorant stick as claimed in claim 1, having a weight-ratio of stearate to palmitate of about 2.75:1 to about 3.25:1.

6. A water-based deodorant stick as claimed in claim 1, further including propylene glycol.

7. A water-based deodorant stick as claimed in claim 1, further including glycerin.

8. A water-based deodorant stick as claimed in claim 1, in which said germicide is 5-chloro-2-(2,4-dichlorophenoxy)phenol.

9. A method for deodorizing human skin comprising applying an effective amount of material from a water-based deodorant stick consisting essentially of:
   (a) from about 3% to about 10% by weight of sodium stearate and sodium palmitate having a weight-ratio of stearate to palmitate of about 1:1 to about 9:1;
   (b) from about 0.1% to about 3.0% by weight of a soap-compatible germicide;
   (c) from about 0.1% to about 0.5% by weight of a compound selected from the class consisting of polyethylene imine and ethoxylated polyethylene imine, said compound having an average molecular weight from about 40,000 to about 100,000; and
   (d) the balance being water.

* * * * *